United States Patent [19]

Newman

[11] Patent Number: 5,616,132

[45] Date of Patent: Apr. 1, 1997

[54] INJECTION DEVICE

[75] Inventor: Duncan Newman, Toronto, Canada

[73] Assignee: Subot, Inc., Toronto, Canada

[21] Appl. No.: 489,455

[22] Filed: Jun. 12, 1995

[51] Int. Cl.⁶ .................................................. A61M 5/178
[52] U.S. Cl. .......................... 604/185; 604/131; 604/140
[58] Field of Search .................................. 604/185, 146,
604/150, 153, 140, 141, 143, 144, 187,
192, 197, 200–202, 204, 212, 236, 263,
415, 131, 93

[56] References Cited

U.S. PATENT DOCUMENTS

| | | | |
|---|---|---|---|
| 4,734,092 | 3/1988 | Millerd | 604/67 |
| 4,886,499 | 12/1989 | Civelli et al. | 604/131 |
| 4,898,583 | 2/1990 | Borsanyi et al. | 604/153 |
| 5,041,094 | 8/1991 | Perego et al. | 604/143 |
| 5,232,448 | 8/1993 | Zdeb | 604/153 |
| 5,242,406 | 9/1993 | Gross et al. | 604/132 |
| 5,281,210 | 1/1994 | Burke et al. | 604/891.1 |
| 5,443,450 | 8/1995 | Kratoska et al. | 604/141 |
| 5,527,288 | 6/1996 | Gross et al. | 604/140 |

*Primary Examiner*—Corrine M. McDermott
*Assistant Examiner*—V. Alexander
*Attorney, Agent, or Firm*—Dowell & Dowell

[57] ABSTRACT

This invention relates to a portable medicant injection device having a diaphragm mounted within its housing and a hypodermic needle that moves in response to the movement of the diaphragm when pressurized gas is released into the housing.

6 Claims, 3 Drawing Sheets

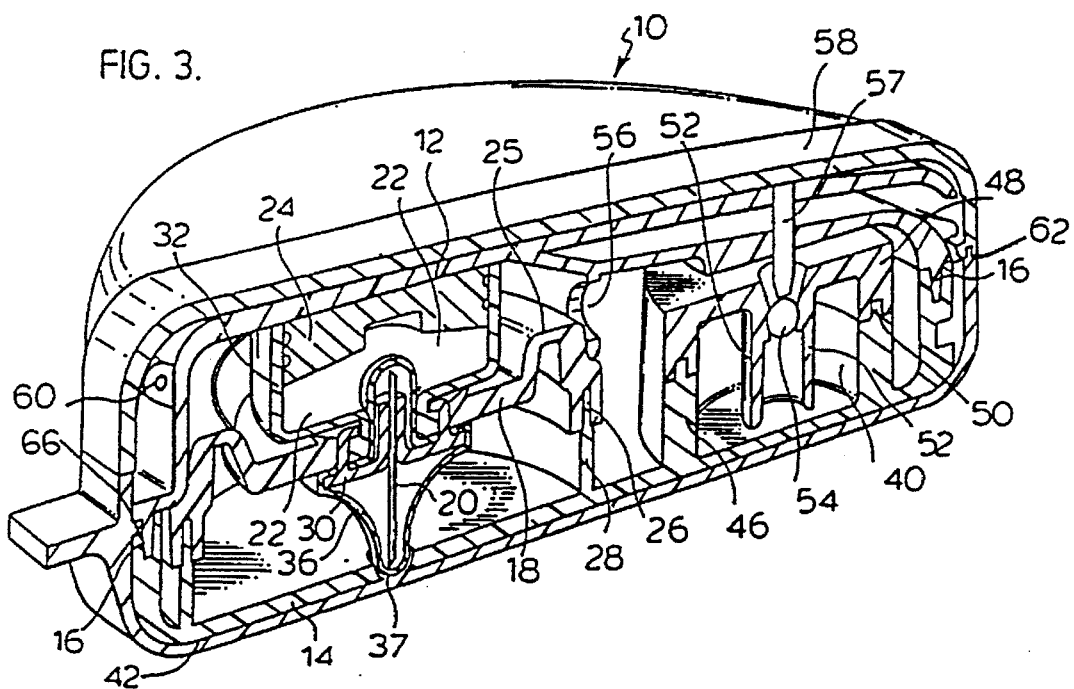
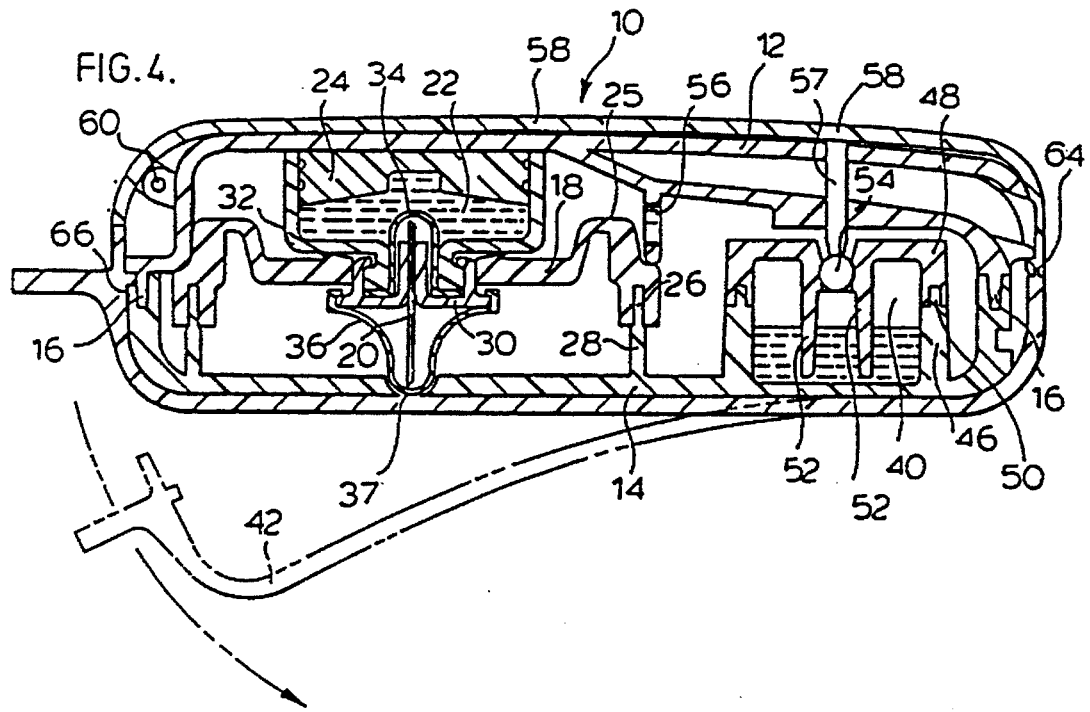

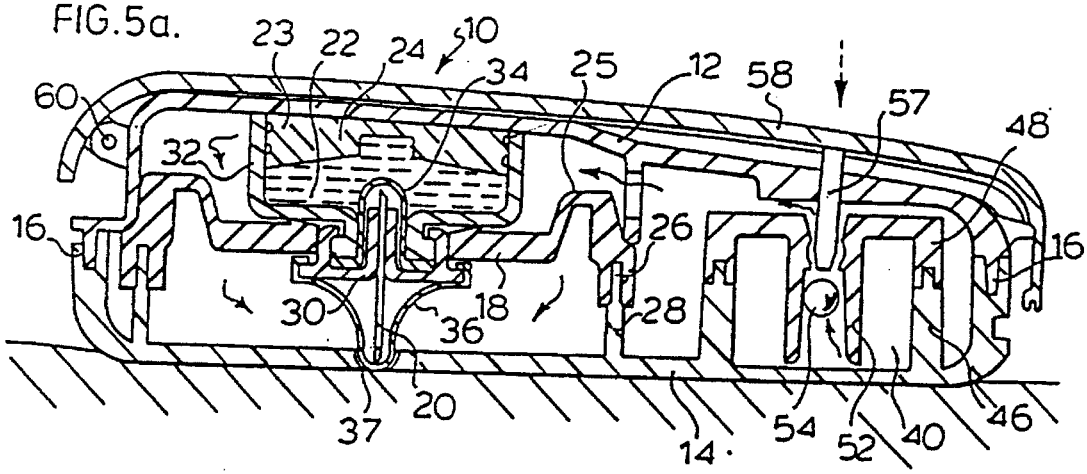
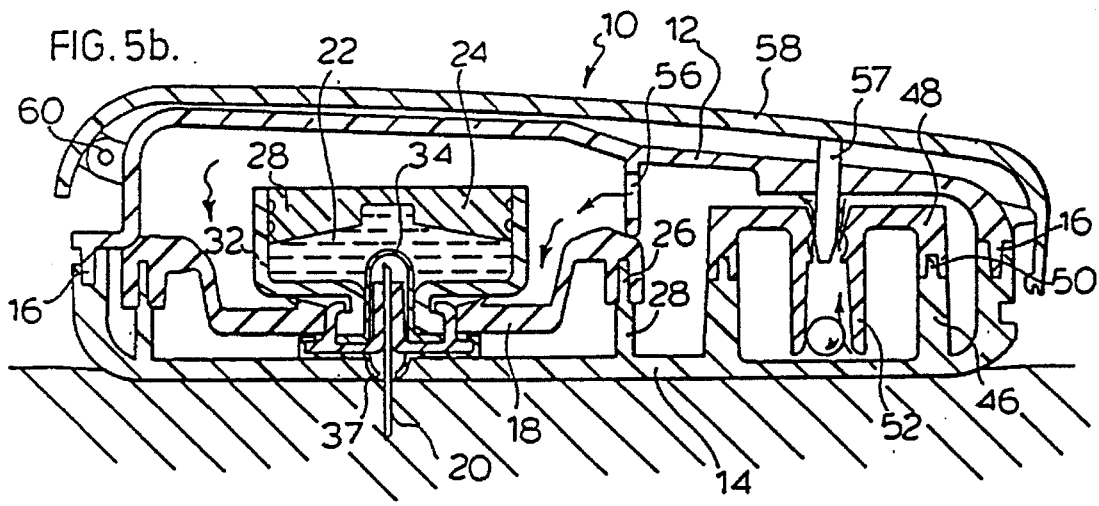
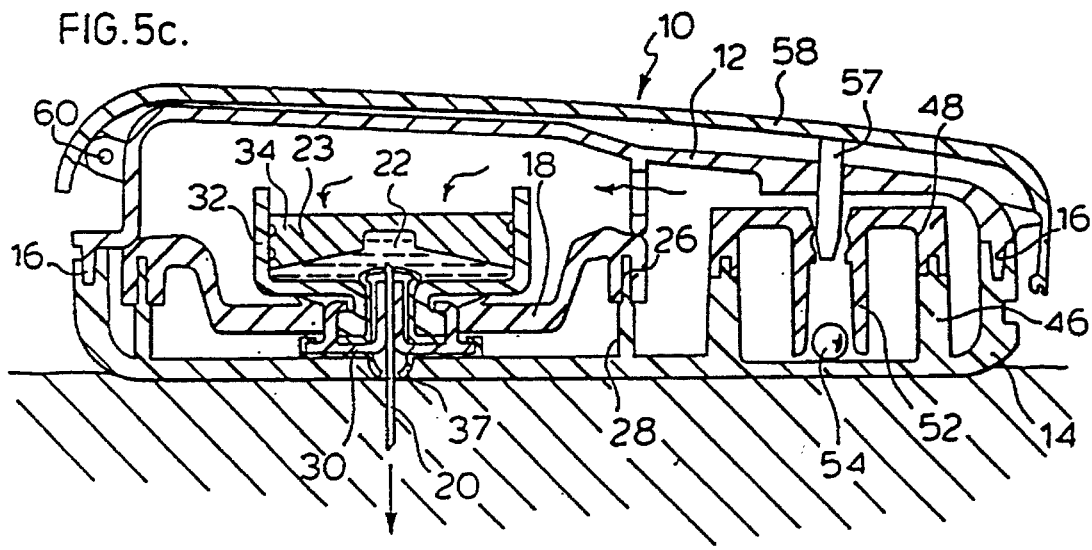

INJECTION DEVICE

BACKGROUND OF THE INVENTION

This invention relates to a medicant injection device of the hypodermic needle type. More particularly, it relates to such a device that is especially suited to self-administration of the medicant. There is a strong demand for such devices and the ones available are not without shortcomings.

They are commonly used by persons with severe allergies. For instance, some persons are allergic to specific foods such as peanut butter, egg whites, walnuts and can become suddenly and seriously ill if they get a small amount of the substance they are allergic to in their food. They become overtaken with a life-threatening swelling of tissue that can in most cases be treated, at least on an emergency basis, with an injection of adrenalin or other anti-histamine. An on-the-spot injection of the appropriate medicant will give them enough time to seek the nearest professional and some persons seriously affected this way carry appropriate medication for hypodermic injection. The medicant injection device of this invention is suitable for this use.

Obvious requirements for a mediant injection device of this service are that it be easy to use because these users are not professional medical people and that it be as inexpensive as possible because these devices are used once and then thrown away.

The injection device most commonly used by allergy suffers is the plunger-cylinder dispenser in various forms, for delivering medicant through a hypodermic needle. However, these devices have proven neither easy to use nor inexpensive. Quite often, the user is not a medical person, and/or is in an excited state of mind. In these cases, the elongated plunger cylinder configuration is cumbersome to hold, difficult to align for injection and difficult to maintain steady in use because of the elongated nature of the device and the smallness of its surface that interfaces with the body. Plunger cylinder needles are also relatively expensive to manufacture.

Reliance on the plunger cylinder type of medicant dispenser in various forms of complexity with its attendant difficulties of use and cost in the single-use/throw-away medicant dispenser has been of long standing.

It is therefore an object of this invention to provide an easy-to-use, inexpensive single user throw-away hypodermic needle medicant injector that overcomes the forgoing problems of the prior art.

This and other useful objects are achieved through the ingenious use of a fluid-operated medicant injection device, that will seat with stability on the body and that has a diaphragm to both carry the needle forward and compress the medicant chamber to discharge the medicant through the needle into the body.

SUMMARY OF THE INVENTION

According to one aspect of the present invention, there is provided in a medicant injection device of the hypodermic needle type: a housing; a diaphragm mounted in the housing for movement between a normal position and an extended position; a hypodermic needle responsive to movement of the diaphragm from its normal position to move between a retracted position and an extended position with respect to the housing; a compressible medicant chamber in medicant-communication, during use, with the hypodermic needle; propellant means comprising a pressurized fluid source in said casing for both moving the diaphragm from its normal position to its extended position and for compressing the compressible medicant chamber; release means for manually releasing pressurized fluid from the pressurized fluid source of the propellant means to move said diaphragm and compress said compressible medicant chamber as aforesaid; said housing having a height and a lower face of dimensions to seat with stability on the skin surface of a patient, in use, with said hypodermic needle in its extended position extending from said lower face.

BRIEF DESCRIPTION OF THE DRAWINGS

The invention will be readily understood after reading the following description of the preferred embodiment in conjunction with a review of the provided drawings in which:

FIG. 3 is a cut-open view of the preferred embodiment showing a perspective view of the inside structure;

FIG. 4 is a cross-sectional view taken along 4—4 of FIG. 1 showing the peeling away of the trigger-locking mechanism before use;

FIGS. 5a, 5b and 5c are cross-sectional views showing the mechanics of the injecting operation.

DETAILED DESCRIPTION OF THE PREFERRED EMBODIMENT

Figure 1:
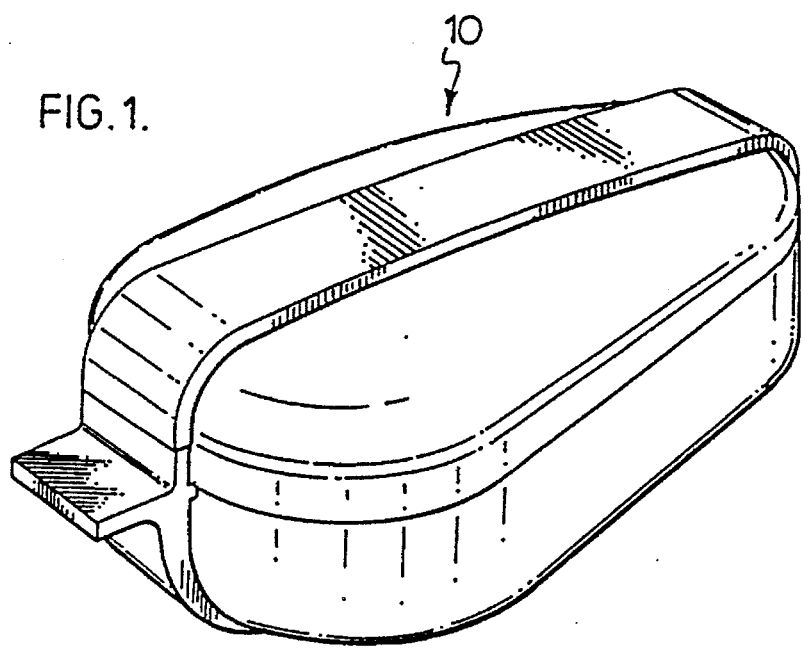
FIG. 1 is a perspective illustration of the preferred embodiment of the present invention.

The drawings illustrate a medicant injection device, generally referred to by the number 10 that has a housing formed from adhesively interconnected upper and lower sections 12, 14 that are cemented together around a circumferentially-extending joint as at 16. Within the housing is mounted a diaphragm 18 for extending the hypodermic needle 20 into the user. The medicant is delivered through the hypodermic needle 20 to the user when plunger 24 compresses medicant chamber 22.

The diaphragm 18 is disc-shaped and formed with a circular rib 25. It is made from a resilient plastics material and has a thickness and size that both provides the structural stability in its normal position of rest and that permits movement, as illustrated in FIGS. 5a, 5b and 5c, to control extension of the needle 20 from the casing. The thickness and size is a design requirement depending on circumstances of use. The inventor has successfully used a diaphragm of two inches diameter having 0.075 inches thickness made out of a polycarbonate material sold under the trade mark LEXAN (a trade mark of General Electric Corporation).

The diaphragm 18 is sealed securely at its peripheral portion to the tongue 26 of wall 28 which extends form the lower housing section 14.

Support member 30 is mounted in sealed relationship to the diaphragm 18 at its center opening. The support member 30 carries both the needle 20 and medicant chamber base cup 32 so that when the diaphragm moves, there is a corresponding movement of the needle 26 and the medicant chamber 22.

Mounted in slidable and sealed relationship with the inner cylindrical wall of the medicant chamber base cup 32 is plunger 24. In combination, the medicant chamber base cup 32 and the plunger 24 define the medicant chamber 22 which houses the medicant. Downward movement of the plunger 24 causes compression of the medicant chamber.

The hypodermic needle 20 is of the standard type used for injection systems. It is hollow to allow for the through-flow of medicant from the medicant chamber 22 in use. Both ends of the needle are shaped to pierce their respective sheaths 34 and 36, which hermetically seal the needle from the medicant and atmosphere during non-use.

Formed in the base of the lower section 14 of the housing 10 is a needle opening 37 through which the needle 20 is extended. In use, the wall of opening 37 is shaped to cause the sheath 36 to be pierced and to guide the needle 20 as it extends from the lower face of the injection device.

A release strip 42 is provided to protect the base of the needle 20 during non-use. When the injector is readied for use, the release strip is removed to expose the opening 27 and the sheath 36.

The movement of the diaphragm 18 in the performance of its function of projecting the needle 20 through sheath 36 and opening 37 and the downward movement of the plunger 24 to compress the medicant chamber 22 and force medicant through the needle 20 in to the body, is illustrated in FIGS. 5a to 5c. It is achieved by a propellant pressurized-fluid contained in chamber 40.

The chamber 40 has a base 46 that is round in cross-section and integrally formed with the lower section 14 of the housing. A cap 48 is sealed to the base 46 around a circumferentially extending tongue and groove joint as at 50 to form the cylindrical chamber with a port tube 52 extending downwardly of the cap 48 Port tube 52 is formed with a seat for a ball valve 54 so that when the chamber 44 is pressurized with fluid, the ball is forced outwardly and against the seat to seal the fluid in the chamber under its own pressure.

The size of the pressurized fluid chamber 44 will depend upon the pressure and the composition of the propellant fluid being stored. The inventor has successfully used a chamber having a volume of five cubic centimeters with liquid isobutane stored at 40 p.s.i. (measured at 20 degrees Centigrade). Generally, the inventor has also found that the use of propellant fluids with boiling points below room temperature work well.

A passage, indicated by numeral 56, is formed in a wall of the housing to permit the flow-through of propellant gas from the pressurized fluid chamber 44 to the diaphragm after the ball valve 54 has been dislodged from its seat in the port tube 52, in operation as will be explained later.

To actuate the diaphragm 18 to extend the needle 20 and cause downward movement of the plunger 24 to force medicant through the needle 20, two preliminary steps are required. Release strip 42 must be removed and the ball valve 54 must be dislodged from its seat in the port tube 52.

The ball valve 54 can be dislodged from its seat by forcing the trigger pin 57 downwardly as illustrated in FIGS. 5a to 5c. Trigger pin 57 extends through an opening in the upper section 12 of the housing 10 and is forced downwardly against ball valve 54 by pressing downwardly on trigger 58. Trigger 58 is a lever hingedly mounted to the upper section 12 of the housing as at 60. Trigger 58 cannot be pressed downwardly if release strip 42 is in place as shown in FIG. 3 because the free end of the trigger is rigidly supported by an end of the release strip as at 62.

Release strip 42 extends longitudinally of the lower section 12 of the housing. It is normally maintained in the position by an interlocking lug and detent at one end as at 64 and by a lug and resilient sloped shoulder at the other end as at 66 and by a pressure-sensitive adhesive. The trigger 58 is normally supported above the height of the trigger pin 56.

After removal of the release strip 42 as shown in FIG. 4, the trigger is now free for rotation about its pivot point in the upper section of the housing to depress the trigger pin as illustrated in FIGS. 5a and 5c.

Figure 2:
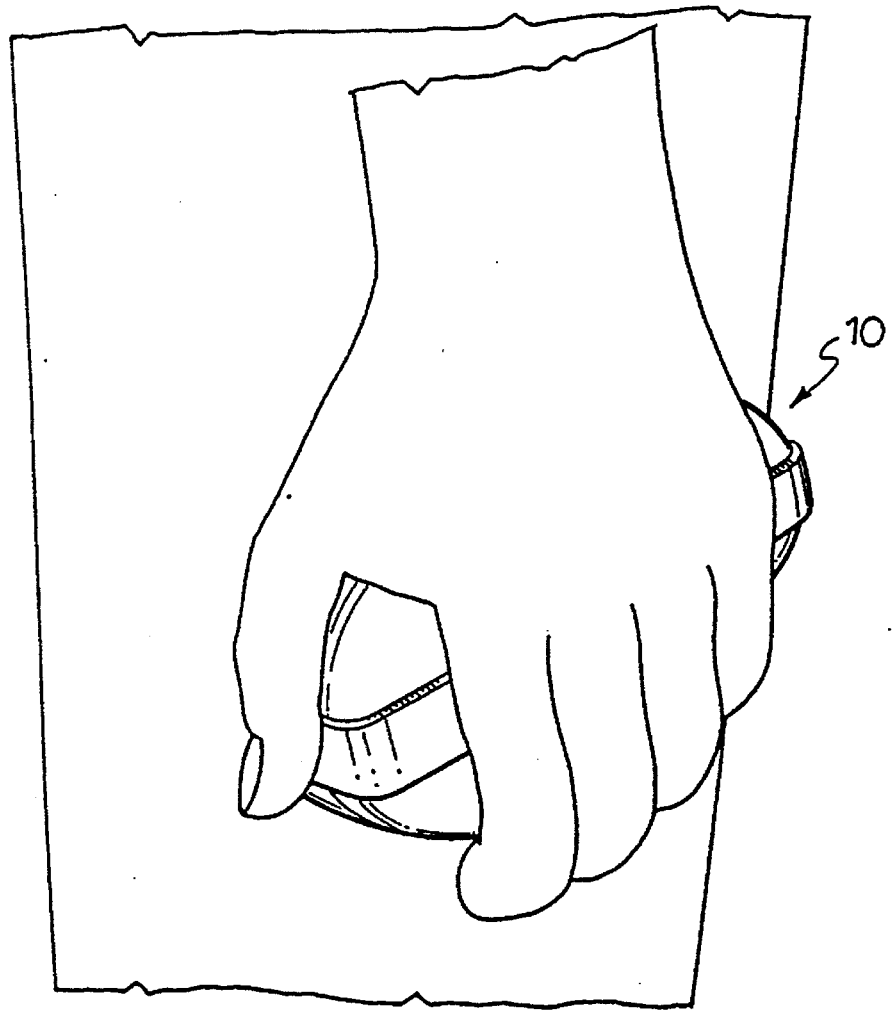
FIG. 2 is a partial view showing the preferred embodiment being carried by a user.

In use, a person likely to require an emergency dosage of medicant would carry a dispenser like the one illustrated in FIGS. 1 and 2 in which the medicant chamber had been filled with his medication and the propellant chamber had been filled with a propellant gas. The medicant is safely stored because the release strip maintains the operating lever a safe height above the trigger pin as noted above.

In the event of need for medicant, the user would flex the release strip 42 downwardly to release the interlock at 66, rotate the loosened end against the holding power of the adhesive as illustrated in FIG. 4 and continue with the rotation until the guard strip separates from the housing. This leaves the trigger 58 free for movement about its pivot 60 on the upper section of the housing and exposes the point of the needle on the underside of the housing.

The user then places the lower free face of the housing on his skin surface with the needle tip overlying the desired location. It will be noted that the lower face of the generally flat housing is of a size that will sit with stability on the skin surface of a user. The user then presses downwardly on the trigger 58 to push the trigger pin 57 downwardly to dislodge the ball valve 54 from its seat. The propellant gas in the chamber 44 rushes out through the port tube 52, through opening 56 and exerts itself against the diaphragm 18. The pressure on the top of the diaphragm forces it downwardly as air on the underside of the diaphragm escapes through a vent port (not shown) to first carry the needle to the position shown in FIG. 5b after piercing sheath 36 and entering the skin of the user. Continued application of pressure on the diaphragm moves the plunger 24 downwardly into the medicant chamber cup 32 as illustrated in FIG. 5c to cause sheath 34 to be pierced and force the medicant from the medicant chamber 22 through the needle 20 and into the user.

After the medicant has been substantially delivered, the pressure on the diaphragm will drop as the fluid chamber 40 becomes exhausted and as propellant gas escapes from the housing to the atmosphere through the space around the trigger pin 56. The pressure in the housing soon approaches atmospheric pressure and the diaphragm returns to its normal position under the influence of its own resilience. As it does so, it withdraws the needle from the patient.

Thus, application of medicant and withdrawal of needle are attended to automatically as a result of applying a simple flat stable device to the skin and depressing a trigger.

Modifications to the preferred embodiment still within the scope of the invention will be readily apparent to those skilled in the art. For instance, instead of using a plunger, the ceiling of the medicant chamber can be defined by the diaphragm with the medicant chamber cup depending therefrom in sealed relationship. Instead of the plunger descending within the cup to compress the medicant chamber, the portion of the diaphragm forming the ceiling of the chamber descends within the cup to compress the medicant chamber. In combination with the plunger embodiment, a safety seal in the form of a second diaphragm can also be placed over the plunger capping the top of the cup 32. The propellant gas, upon being released into the chamber, would depress the second diaphragm into the cup, forcing the plunger 24 downwardly and compressing the medicant chamber 22.

In yet another embodiment (not shown), a second diaphragm can be mounted to cover the opening of the cup and replace the plunger. In use, instead of the plunger descending within the medicant cup to compress the medicant chamber, the second diaphragm is pressed into the cup to compress the medicant chamber.

In yet another embodiment (also not shown), a second diaphragm can be used as a seal for the medicant cup, being placed over the plunger to cover the cup. In use, the diaphragm and the plunger descend together within the medicant cup to compress the medicant chamber.

It is not intended that this specification be read in a limiting sense. The embodiment illustrated and described is the preferred embodiment only and it is contemplated that the inventive concept of a diaphragm may be incorporated into other types of medicant injectors within the scope of the invention and as claimed in the appended claims.

I claim:

1. In a medicant injection device of the hypodermic needle type:

a housing;

a diaphragm mounted in the housing for movement between a normal position and an extended position;

a hypodermic needle mounted within the housing and operatively connected to the diaphragm for movement whereby the hypodermic needle is responsive to movement of the diaphragm from its normal position to move between a retracted position and an extended position with respect to the housing;

at least one chamber wall defining a compressible medicant chamber within the housing, said compressible medicant chamber being in medicant-communication, during use, with the hypodermic needle;

propellant means comprising a pressurized fluid source in said housing for both moving the diaphragm from its normal position to its extended position to thereby cause a responding movement of the hypodermic needle from its retracted position as aforesaid and for compressing the compressible medicant chamber to cause medicant to be delivered through the hypodermic needle;

release means for manually releasing pressurized fluid from the pressurized fluid source of the propellant means to move said diaphragm and compress said compressible medicant chamber as aforesaid;

said housing having a height and a lower face of dimensions to seat with stability on the skin surface of a patient, in use, with said hypodermic needle in its extended position extending from said lower face.

2. In a medicant injection device as claimed in claim 1:

in which said medicant chamber is carried by said diaphragm and is at least partly defined by said diaphragm.

3. A medicant injection device as claimed in claim 2:

in which the compressible medicant chamber is located between the diaphragm and the lower face of the housing and is responsive to movement of the diaphragm from its normal position to compress and force medicant therefrom through the hypodermic needle as the diaphragm moves from its normal position to its extended position.

4. In a medicant injection device as claimed in claim 1:

in which said diaphragm has a resilient characteristic that under atmospheric pressure conditions returns it to its normal position from its extended position.

5. In a medicant injection device as claimed in claim 1:

in which one of said at least one chamber wall of the compressible medicant chamber is formed by a cup, said cup having a top opening sealed with a portion of said diaphragm.

6. In a medicant injection device as claimed in claim 1:

in which the compressible medicant chamber is located between the diaphragm and the lower face of the housing and is responsive to movement of the diaphragm from its normal position to compress and force medicant therefrom through the hypodermic needle as the diaphragm moves from its normal position to its extended position.

* * * * *